United States Patent [19]

Babasade

[11] Patent Number: 5,437,410
[45] Date of Patent: Aug. 1, 1995

[54] PASSIVE FRAGRANCE DISPENSER

[75] Inventor: Wolfgang Babasade, New Milford, N.J.

[73] Assignee: ISC, Inc., Mahwah, N.J.

[21] Appl. No.: 262,780

[22] Filed: Jun. 20, 1994

[51] Int. Cl.⁶ .............................................. A61L 9/04
[52] U.S. Cl. ...................................... 239/55; 239/45; 239/58; 206/7
[58] Field of Search ..................... 239/44, 45, 55, 56, 239/58, 34; 206/17

[56] References Cited

U.S. PATENT DOCUMENTS

| | | | |
|---|---|---|---|
| D. 220,488 | 4/1971 | Patrigot | D23/150 |
| 472,133 | 4/1892 | Merrill . | |
| 2,500,896 | 3/1948 | Drake | 299/20 |
| 2,784,529 | 3/1957 | Prestigiacomo | 239/55 X |
| 3,613,994 | 10/1971 | Goodman | 239/44 |
| 5,156,334 | 10/1992 | Kimbell et al. | 239/34 |
| 5,314,669 | 5/1994 | Hamilton | 239/58 X |

FOREIGN PATENT DOCUMENTS

| | | | |
|---|---|---|---|
| 2506173 | 11/1982 | France | 239/34 |
| 6601170 | 1/1966 | Netherlands | 239/34 |

*Primary Examiner*—Andres Ashnikow
*Assistant Examiner*—Kevin Weldon
*Attorney, Agent, or Firm*—W. Patrick Quast

[57] ABSTRACT

A passive aromatic substance dispenser is described. A highly absorbent rod shaped wick, held within a hermetically sealed tube, serves as a fragrance dispensing reservoir in contact with an efficient fragrance diffuser, and also serves as a convenient means for suspending the diffuser in a selected area to be fragranced. When fragrancing an area is not desired, closing the housing for the diffuser seals the diffuser from ambient air currents, protecting the aromatic substance from evaporating from the diffuser. The vacuum that develops within the tube due to the absorption of aromatic substance from the rod and into the diffuser prevents draining of the fragrance material from the rod and into the diffuser when not required, thus providing self regulation of the fragrance material by the dispenser.

8 Claims, 5 Drawing Sheets

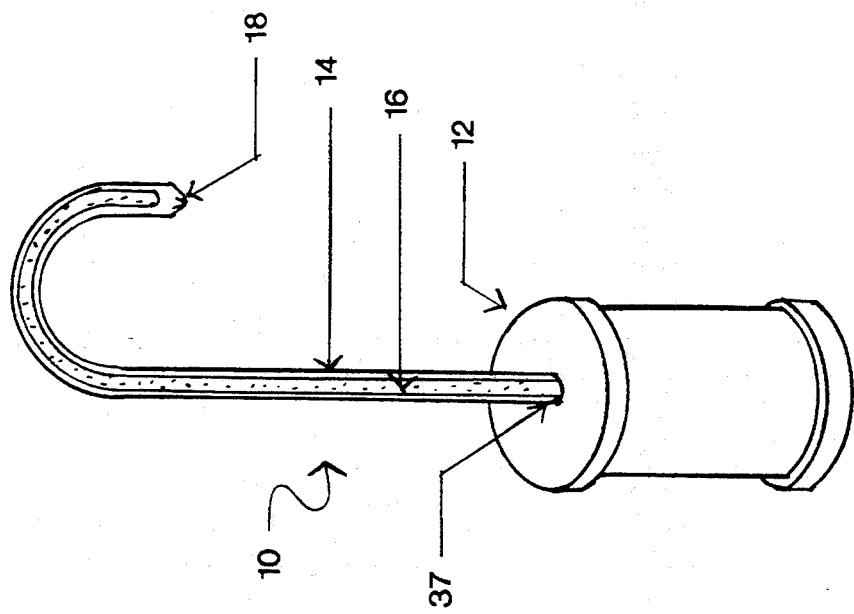
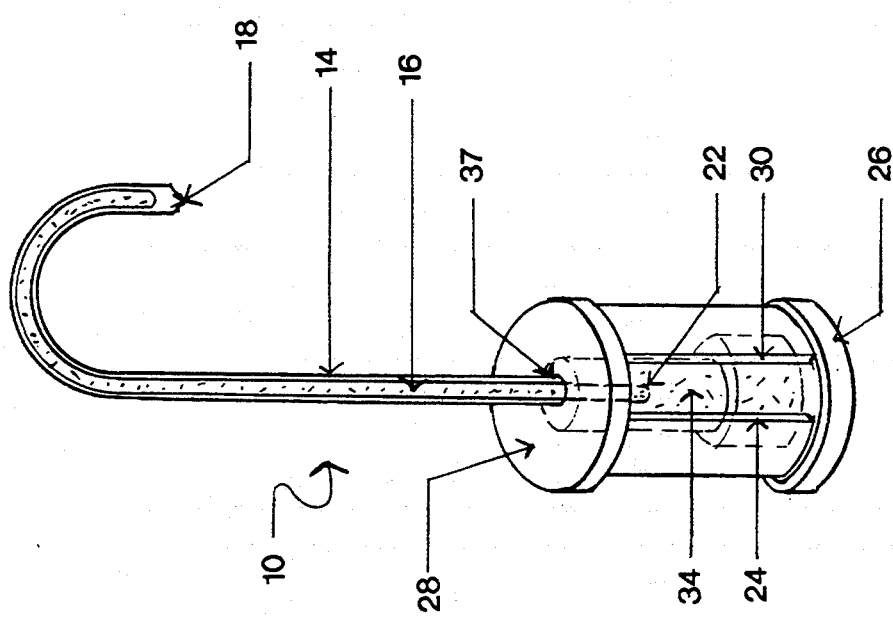

PASSIVE FRAGRANCE DISPENSER

BACKGROUND

This invention relates to aromatic substance dispensers and in particular to passive fragrance dispensers.

By passive fragrance dispenser it is meant a device for fragrancing an area wherein the fragrance emitting substance is simply exposed to normal air currents within an environment to dispense the fragrance in vapors throughout the area without resorting to fans, jet sprays, heating devices, and so on. Many devices of this type are currently in use or have been proposed. For example, U.S. Pat. No. 355,982 teaches the use of a hollow stem being immersed at one end in a liquid fragrance material containing reservoir, having an artificial flower connected at its other end, the hollow stem being filled with an absorbent material. In this case a liquid fragrance material is carried by capillary action from the liquid fragrance material reservoir to the artificial flower by means of the absorbent wick.

U.S. Pat. No. 472,133 teaches using a liquid fragrance material reservoir and absorbent wick in combination with a movable perforated cover to provide means for valving vapor release.

In U.S. Pat. No. 2,500,896 a controllable aromatic dispenser is disclosed. A liquid reservoir feeds fragrance material to a wick which can be controllably exposed to an external air stream by means of rotatable perforated discs. This invention further discloses an elongated bracket having a hooked end for suspending the dispenser in an air stream. U.S. Pat. No. 220,488 depicts a perfume evaporator for automobiles having a chain presumably for convenient hanging within an automobile.

While the above described aromatic substance dispensers provide convenient means for fragrancing an area they do not disclose the uniquely controlled fragrance delivery system of the instant invention. The passive dispenser herein described does away with liquid reservoirs and there attendant problems by making a highly absorbent wick material, threaded within a tube, perform the double function of a fragrance substance reservoir as well as a convenient means for suspending the fragrance dispenser of the invention within the environment to be fragranced. Delivery of fragrance material from the wick to a diffuser within the dispenser is uniquely controlled by a partial vacuum created by the flow of fragrance material out of the wick and into the diffuser. By this means an economical and long lasting self regulating passive fragrance dispenser is provided.

Accordingly, the primary object of the invention is to provide an economical, controlled passive fragrance dispenser.

An additional object of the invention is to provide a passive fragrance dispenser which does not make use of a liquid reservoir.

A further object of the invention is to provide a passive fragrance dispenser wherein access to fragrance vapors can be sealed.

Still another object of the invention is to provide a self regulating passive fragrance dispenser.

An additional object of the invention is to provide an efficient passive fragrance dispenser for a small environment, such as the interior of an automobile.

SUMMARY

These and other objects are obtained with the instant invention of a passive fragrance dispenser.

Typical currently available passive fragrance dispenser systems usually make use of a liquid fragrance material reservoir and a wick. The wick usually acts as the fragrance vapor diffuser, being connected to the liquid reservoir and then extending upwards above the reservoir, the liquid fragrance material within the reservoir being drawn by capillary action into the wick, and then being dispensed via ambient air currents to fragrance an immediate environment. Various methods have been proposed to control leakage of liquid from the liquid from the reservoir, and to control vaporization of fragrance material from a wick, as has been previously noted.

In the instant invention the wick itself performs the double function of both acting as a reservoir for a liquid fragrance material, and as a convenient means for suspending a fragrance vapor diffuser within the ambient air streams of particular environments. For example, in one version of the invention a wick material is threaded into an elongated, polyvinylchloride plastic tube, the tube being many times greater in length than in width. The wick material can be, for example, POREX (a registered trademark of Porex Technologies, 500 Bohannon Road, Fairburn, Ga. 30213-2828). POREX is composed of polyethylene granules having a specific porosity, said granules being capable of being formed or sintered into required shapes. In this case the POREX is formed into the shape of a rod which is threaded into the PVC tube. The POREX rod preferably stops short of one end of the PVC tube, and extends a spaced distance from the other end of the PVC tube.

This end assembly of the tube and rod, i.e. the end of the tube from which the rod protrudes, is then secured within a fragrance vapor diffuser. The diffuser can be generally cylindrical in shape, and can also be fabricated from POREX. Finally, a two piece grid assembly envelopes the fragrance vapor diffuser. The grid assembly can be in the shape of two concentric approximate ½ cylinders, one of said ½ cylinders being secured to the other ½ cylinder so that when in the form of a full cylinder the diffuser is enclosed, sealing it off from ambient air currents. A liquid fragrance material is then injected into the open end of the PVC tube, and this open end is then crimped shut in an air tight manner.

The end portion of the PVC tube having the crimped closure can be bent into a hook shape to provide a convenient means for suspending the passive fragrance dispenser in an area. The passive fragrance dispenser of the invention can be suspended from the supporting rod on the rear view mirror of an automobile. An additional convenience for this and other placement areas is to coat the exterior surface of the PVC tube with a phosphore coating so that it will glow in the dark.

After the passive fragrance dispenser is suspended in a selected environment, the immediately surrounding area can be fragranced by turning the movable outer cylinder so that the POREX diffuser is exposed to ambient air currents. Under the influence of gravity and capillary action the now absorbed liquid fragrance material within the POREX rod migrates into the POREX diffuser, and the fragrance material then evaporates into the environment.

When fragrancing an area is not desirable, the movable ½ cylinder on the grid assembly enveloping the diffuser is rotated so as to provide a full cylindrical housing for the POREX diffuser. Under these storage conditions, the unique self regulating fragrance material dispenser mechanism of the invention becomes of crucial importance. The POREX diffuser is, of course, an efficient, high capacity fragrance material absorber. Simply allowing gravity and capillary forces to continue to act during storage without interference would rapidly drain the POREX rod of its absorbed liquid fragrance material, rendering the POREX rod ineffective as a long term "reservoir" of fragrance material. In the instant invention, however, as fragrance material migrates from the POREX rod and into the POREX diffuser a partial vacuum is created within the tube containing the POREX rod. This partial vacuum prevents additional migration of the absorbed liquid fragrance material into the diffuser until the movable approximate ½ cylinder portion of the grid assembly holder is rotated to expose the diffuser to ambient air currents.

In this manner a simple to manufacture, economical, self regulating passive aromatic substance dispenser is provided. Fragrance material is efficiently fed into the diffuser when required, and when not required the partial vacuum serves to maintain the original charge of the liquid fragrance material within the POREX rod wick, which in this case is acting as an efficient, leak proof, double function, long term "reservoir" for the fragrance material.

BRIEF DESCRIPTION OF THE DRAWINGS

FIG. 3 is a perspective view of one version of the invention in operation, with the diffuser exposed to ambient air currents.

FIG. 4 is a perspective view of one version of the invention with the grid assembly housing for the diffuser in closed position.

DETAILED DESCRIPTION

Figure 1:
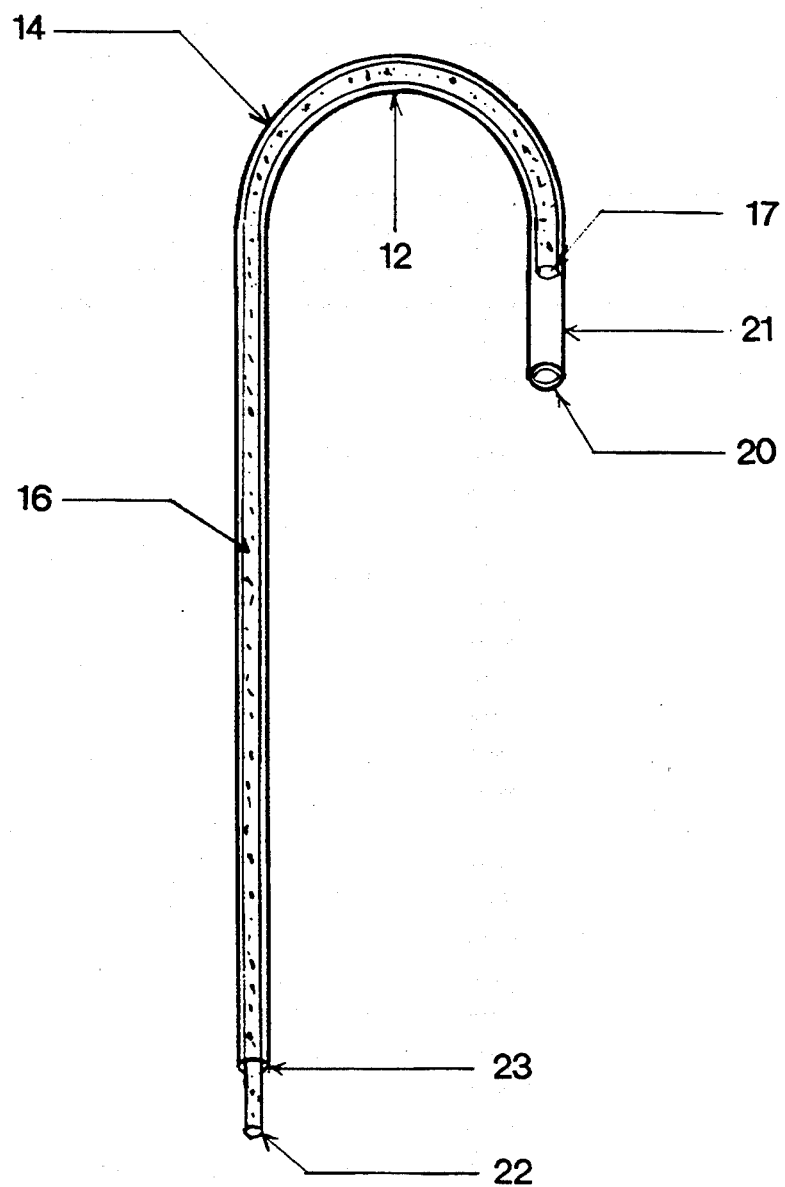
FIG. 1 illustrates a formed rod, acting as a combination fragrance material wick and reservoir, having been placed within a tube.

Referring now to the drawings, in FIG. 1 a tube 14 is shown having a rod 16 threaded within it. One end of the rod 22 extends beyond a first end 23 of the tube, both ends of the tube 14 being open at this time, before assembly into a version of the complete passive fragrance dispenser 10 (FIG. 3) of the invention. The other end of the rod 17 ends a spaced distance 21 short of the second end 20 of the tube. The tube 14 can be made out of glass, metal, or plastic, in this case polyvinylchloride being selected as a preferred material since it can easily be formed with a portion of the tube in the shape of a hook 12, and first end 23 can be connected to a housing, and second end 20 can be hermetically crimped shut as will be more fully explained.

The rod 16 serves the double function of a wick for absorbing liquid aromatic materials, and acting as a reservoir for these aromatic materials. The rod 16 can be fabricated from a variety of absorbents, in this case POREX being considered particularly well suited to this application. POREX is porous polyethylene granules with an average pore size in this selected instance of approximately 40%. Thus POREX is capable of absorbing a large volume of a liquid aromatic material, and providing for efficient delivery of said aromatic material under favorable conditions of gravity and capillary action.

Figure 2:
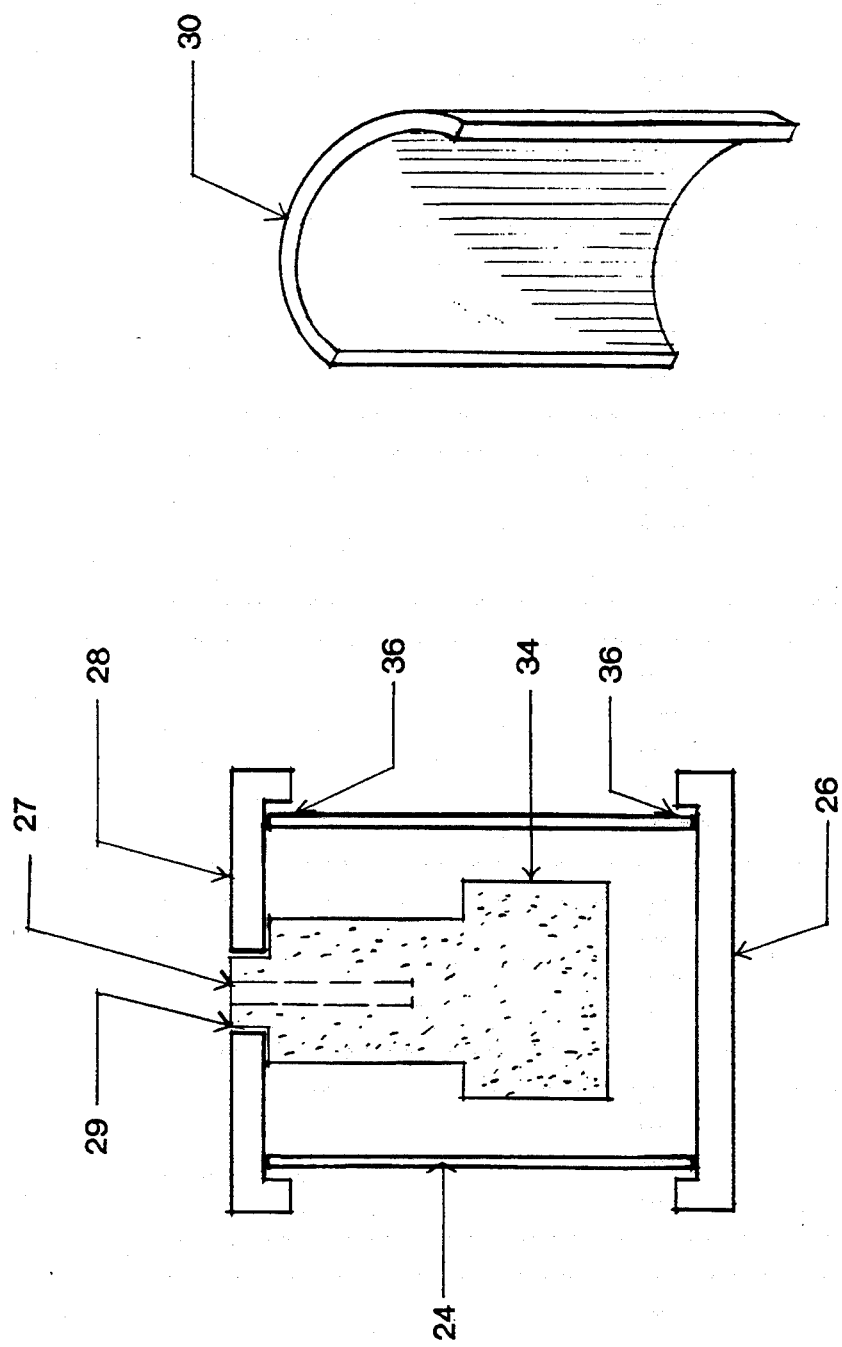
FIG. 2 is an exploded view of the grid assembly holder for the diffuser.
Figure 2B:
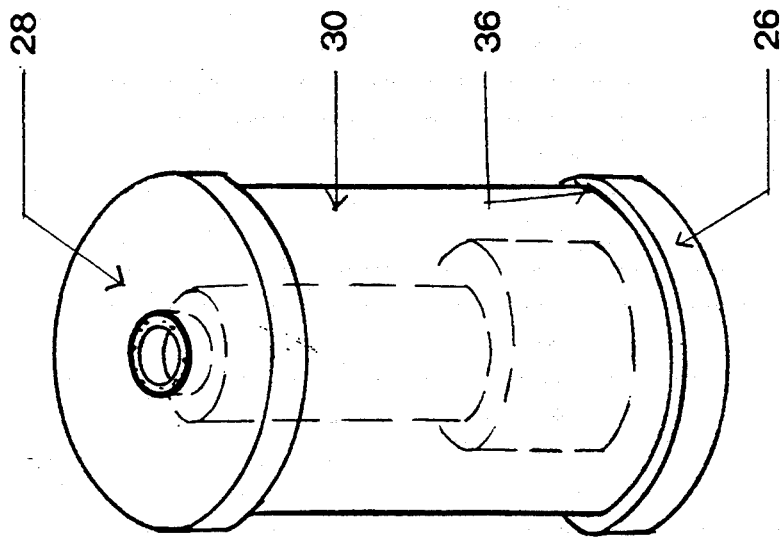
FIG. 2B illustrates the partial cylinders comprising the grid assembly housing in closed position, enveloping the diffuser.
Figure 2A:
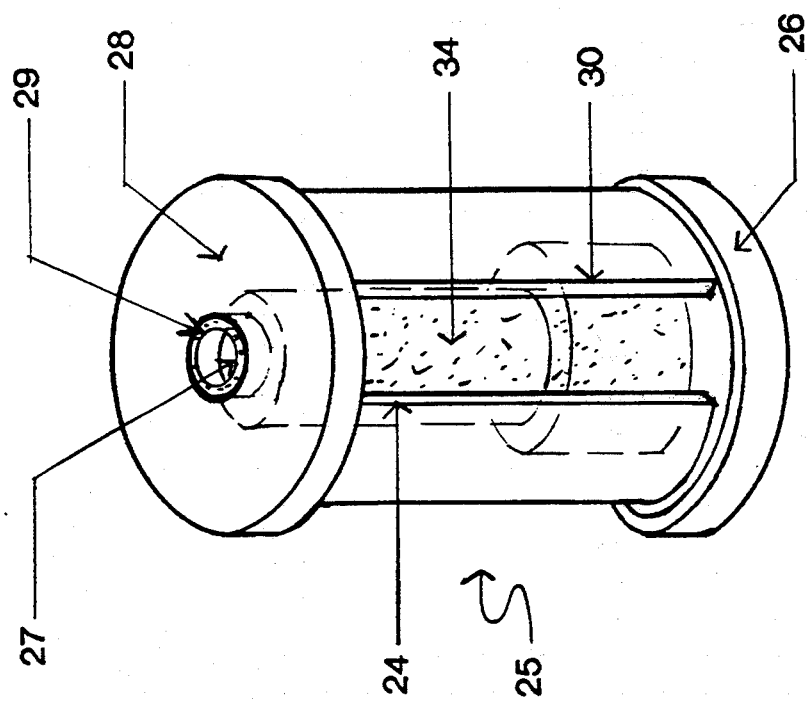
FIG. 2A illustrates the partial cylinders comprising the grid assembly housing in open position, exposing the diffuser to ambient air currents.
Figure 5:
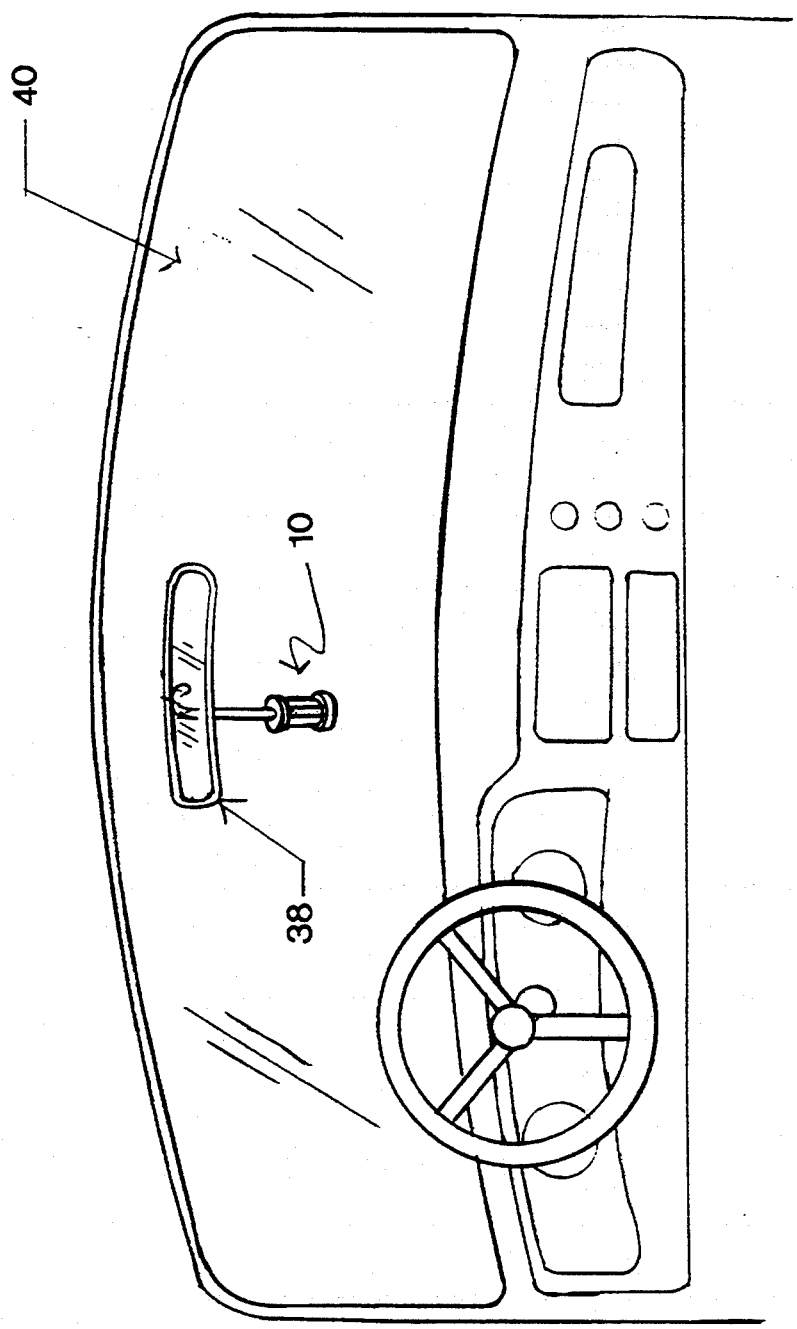
FIG. 5 shows one version of the invention in place suspended from the rear view mirror of an automobile.

In FIGS. 2, 2A and 2B the housing 25 into which the unshielded portion of the rod 16 is to be inserted, and the tube 14 to be affixed to, is illustrated. The housing 25 can consist essentially of two approximate ½ cylindrically shaped sections (24,30 FIG. 2), with a first ½ cylinder section 24 having a full circular top plate 28, and a full circular bottom plate 26. Both plates 26,28 being identical to each other except for their position, and both having a slightly larger diameter than the diameter of the first ½ cylinder 24. Each of the plates 26,28 has a circular groove 36 on the underside of its periphery. The second approximate ½ cylinder 30 encompasses an area slightly greater than a half cylinder. This second approximate ½ cylinder section 30 then snap fits into the grooves 36 in the underside of the top 28 and bottom 26 circular plates of the first ½ cylinder section 24.

As can be seen in FIGS. 2, and 2A the housing 25 contains a diffuser 34. The diffuser is held in place by cementing the diffuser to the wall 29 at the opening 27 to the housing. The diffuser must also be fabricated in an efficient absorbent material. The above described POREX being employed in this example.

FIGS. 2A and 2B illustrate the functioning of the assembled housing 25. The second approximate ½ cylinder 30 slides within the grooves 36 of the first half cylinder 24, being capable of largely exposing the diffuser 34 to ambient air currents, or to seal the diffuser from ambient air currents when it is fully rotated in the opposite direction.

FIG. 3 illustrates one version of the completely assembled passive fragrance dispenser of the invention. The unsheathed portion of the rod 16 has been pushed into the diffuser 34. The tube 14 is cemented to the housing 25 at a point 37 immediately adjacent the first end 23 of the tube. The second end 20 of the tube is now shown as being crimped shut 18 in order to provide an hermetic seal within the tube 14. Prior to crimping this end shut, approximately 1.4 grams of a selected liquid fragrance material is injected into this second open end 20 of the tube 14 so as to saturate the rod 16 with an appropriate fragrance material.

In FIG. 4 the complete assembly of one version of the fragrance dispenser 10 of the invention is shown, with the second end 20 of the tube 14 crimped shut 18, the tube 14 cemented 37 to the housing, and the two approximate ½ cylindrical sections of the housing being in closed position so as to provide a seal for the diffuser 34 within said housing. Under these conditions a portion of the aromatic material within the rod will migrate, under the influence of gravity and capillary action, into the diffuser. Under these sealed conditions, as aromatic material migrates out of rod 16, a partial vacuum is created within tube 14. This vacuum now acts as a counter force to said gravity and said capillary action, preventing further absorption of the original charge of the liquid aromatic material into the diffuser.

When it is desirable to fragrance an area, as, for example, the interior of an automobile, the passive fragrance dispenser is simply hung by the hook shape 12 of the tube 14 on the windshield 40 of the automobile, making use of the rear view mirror 38 attached to the windshield. Rotating the two concentric halves 24, 30 of the housing 25 exposes the diffuser 34 to ambient air currents within the automobile (not shown). Under these conditions aromatic material evaporates from the diffuser, efficiently fragrancing the selected area. The diffuser 34 will continue to absorb additional fragrance material from the rod 16 in order to replace the evaporated fragrance material. When fragrancing is no longer required the movable section 30 of the housing is rotated so as to shut off the diffuser from ambient air currents. Once again, under this sealed condition, the partial vacuum within the tube 14 prevents further absorption of aromatic material from the rod 16 and into the diffuser 34.

Thus an economical, self regulating fragrance dispenser is provided by the instant invention. Efficient area fragrancing is assured by the cooperation of the diffuser and the rod. At the same time extended use of the fragrance dispenser is obtained by preventing the draining of the fragrance material from the rod and into the diffuser when the fragrance dispenser is not in use, and is in a stand by condition.

While the present invention has been disclosed in connection with a version shown and described in detail, various modifications and improvements thereon will become readily apparent to those skilled in the art. Accordingly, the spirit and scope of the present invention is to be limited only by the following claims.

What is claimed is:
1. An aromatic substance dispenser, comprising:
   (a) a housing containing a diffuser;
   (b) said diffuser being capable of absorbing quantities of said aromatic substance and thence to diffuse vapors of said aromatic substance into a surrounding environment;
   (c) a first end of a tube being placed within and secured to said housing;
   (d) a rod being placed within said tube, said rod extending throughout most of the length of said tube;
   (e) said rod extending a distance beyond said first end of said tube into said housing and in contact with said diffuser, the other end of said rod terminating within said tube from a second end of said tube, said second end of said tube being external to said housing;
   (f) said rod and said diffuser being made of an absorbent material capable of absorbing said aromatic substance;
   (g) said housing having means for totally enclosing said diffuser from the surrounding environment when diffusing of said aromatic substance to said environment is not required, and said housing having means for partially exposing said diffuser to said surrounding environment when diffusing of said aromatic substance to said environment is required;
   (h) said tube having means for admitting a liquid quantity of said aromatic substance at said second end of said tube so that under the influence of gravity and capillary action said rod is saturated with said aromatic substance;
   (i) means for sealing said second end of said tube after said liquid quantity of said aromatic substance has been admitted to said tube; and
   (j) said absorbent material within said diffuser absorbing said aromatic substance from said rod by said gravity and said capillary action, so that when it is required to diffuse said aromatic substance to said surrounding environment activating said housing means for partially exposing said diffuser to said surrounding environment causes said aromatic substance to be diffused into said surrounding environment.

2. The aromatic substance dispenser according to claim 1 wherein activating said housing means for totally enclosing said diffuser seals said diffuser from ambient air currents within said surrounding environment, so that as said diffuser absorbs said aromatic substance from said rod a partial vacuum is created within said tube, said partial vacuum then preventing further absorption of said aromatic substance from said rod into said diffuser; and activating said housing means for partially exposing said diffuser to said environment exposes said diffuser to said air currents, causing said aromatic substance to evaporate from said diffuser, said diffuser continuing to replace said evaporated aromatic substance by continuing to absorb said aromatic substance from said rod under the influence of said gravity and said capillary action while said diffuser is diffusing said aromatic substance to said surrounding environment.

3. The aromatic substance dispenser according to claim 2 wherein said rod is formed from porous polyethylene granules.

4. The aromatic substance dispenser according to claim 2 wherein said diffuser is formed from porous polyethylene granules.

5. The aromatic substance dispenser according to claim 2 wherein said housing consists of two solid walled sections forming a seal for said diffuser, a first section being immovable relative to a second section, said second section being movable relative to said first section, so as to partially expose said diffuser when said second section is moved to an open position relative to said first section, said housing forming a seal for said diffuser when said second section is moved to a closed position relative to said first section.

6. The aromatic substance dispenser according to claim 2 wherein a portion of said tube immediately adjacent said second end is formed into the shape of a hook for hanging said dispenser in an upright position from an available projection.

7. The aromatic substance dispenser according to claim 6 wherein said hook is adapted to conveniently fit over a support member of a rear view mirror in an automobile.

8. The aromatic dispenser according to claim 2 wherein said tube is coated with a phosphorescent coating.

* * * * *